United States Patent [19]
Adams

[11] 4,096,852
[45] Jun. 27, 1978

[54] SKIN CONDITIONING INDICATOR
[75] Inventor: Guy Adams, Monroe, N.Y.
[73] Assignee: Solitron Devices, Inc., Tappan, N.Y.
[21] Appl. No.: 753,536
[22] Filed: Dec. 22, 1976
[51] Int. Cl.² .............................................. A61B 5/00
[52] U.S. Cl. ................................ 128/2 H; 128/2.1 Z; 73/342
[58] Field of Search ................... 128/2 H, 2 R, 2.1 Z, 128/2.1 E, 2.1 C, 2.1 R; 73/340, 341, 342; 273/1 F

[56] References Cited
U.S. PATENT DOCUMENTS

| 2,728,337 | 12/1955 | Guillemin, Jr. | 128/2 H |
| 3,593,704 | 7/1971 | Schwab | 128/2 H X |
| 3,699,813 | 10/1972 | Lamb | 128/2 H X |

FOREIGN PATENT DOCUMENTS

| 271,100 | 6/1965 | Australia | 128/2 H |
| 1,605,392 | 2/1975 | France | 128/2 H |
| 2,250,505 | 6/1975 | France | 73/340 |
| 662,033 | 6/1938 | Germany | 128/2.1 R |
| 2,209,973 | 9/1972 | Germany | 128/2 H |

OTHER PUBLICATIONS

Edmonds et al., "A Simple Millivoltmeter & Electrodes..." Med. & Biol. Eng., vol. 8, No. 4, pp. 409–410, 1970.

Primary Examiner—Robert W. Michell
Assistant Examiner—Lee S. Cohen
Attorney, Agent, or Firm—Richard G. Geib

[57] ABSTRACT

A circuit for an indicator having a constant current temperature measuring circuit that can be balanced so as to provide a norm on an indicator so that any excursion thereof therefrom would provide indication of the need for emollients or astringents in proper care of the skin.

4 Claims, 3 Drawing Figures

SKIN CONDITIONING INDICATOR

BACKGROUND

Nothing is known to exist in the marketplace to assist one in deciding what is needed for proper skin conditioning. It is to fill this void that this invention is of particular utility. More particularly this invention was conceived in order to adapt solid state technology to the problem of investigating into the condition of ones skin and indicating whether it is too supple and in need of an astringent or whether it needs an emollient to make the skin smoother.

More specifically this invention is concerned with using constant current devices in a type of Wheatstone bridge circuit with a probe that will use resistance as a means to unbalance the circuit so that an indicator can alert one to the type of skin treatment that would then be best to employ.

DRAWING DESCRIPTION

DETAILED DESCRIPTION

Figure 1:
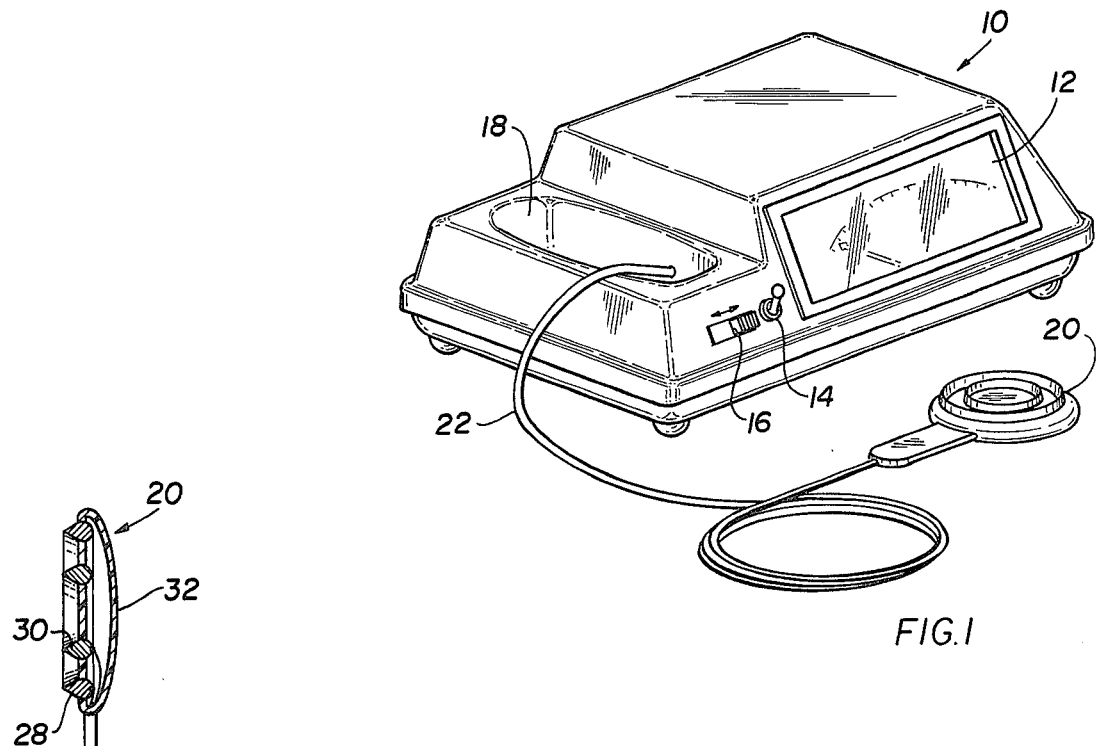
FIG. 1 is an isometric of an apparatus embodying this invention.

With more particular reference now to FIG. 1, there is shown thereby a housing 10 having an indicator 12 on a face thereof above an on-off switch toggle 14 and a calibration switch slide 16. A pocket 18 is provided along one side within which a probe 20 (shown outside same for drawing clarity) is normally stowed, along with cord 22 connecting the probe 20 to a circuit within the housing.

Figure 2:
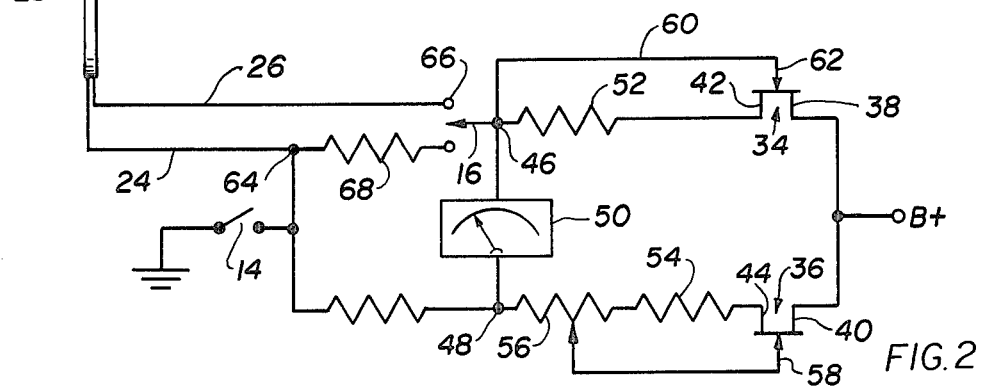
FIG. 2 is a specific circuit diagram of the circuit employed in the apparatus of FIG. 1.

This connection and circuit are more specifically detailed in FIG. 2 where cord 22 is shown to have its two leads 24 and 26 connected to respective, concentric rings 28 and 30 in the dielectric material, such as plastic, body 32 of the probe 20. This body 32 is shown approximately full size so as to illustrate that it may be held in the palm of ones hand and yet probing a defined area of skin between rings 28 and 30 so as to bring the electrical resistance of such area into an electrical circuit.

The electrical circuit aforementioned is chosen to employ constant current semiconductors (i.e. field effect transistors, FET's) 34 and 36 so as to have their drain terminals 38 and 40 connected to a positive potential B+ of a source of electrical energy. This connection could be to a DC battery source by a selective diode circuit such as shown by U.S. Pat. No. 3,993,043 assigned to the common assignee hereof. FET's 34 and 36 have their source terminals 42 and 44 connected by resistance means to indicator terminals 46 and 48 of indicator 50. Actually the FET's 34 and 36 are employed in a bridge circuit with fixed resistances 52 and 54, variable resistance 56 operably connected to gate 58 of FET 36, and lead 60 connecting gate 62 of FET 34 to terminal 46. It may be appreciated by one skilled in the art that such a circuit will be possible of variable control to balance the source flow through each leg and the switch when toggle 14 is closed contrary to normal bridge circuits, however, is the fact that FET's 34 and 36 being insensitive to temperature excursions the circuit is better capable of detecting changes of temperature by probing therefor as a function of varying resistance. Therefore, a probe 20, having rings 28 and 30 spaced by the dielectric body 32, can, when placed in each leg about indicator 50, as by connection of leads 24 and 26 to terminals 64 and 66, operate the indicator 50 in accordance with the temperature (resistance), a function of suppleness, of the skin tissue between rings 28 and 30, being held against ones face by the palm of the hand.

The balancing of this circuit will have first been completed by switching calibration resistance 68 in the circuit with slide 16 and pot 56 adjusted with the gate of FET 36.

Figure 3:
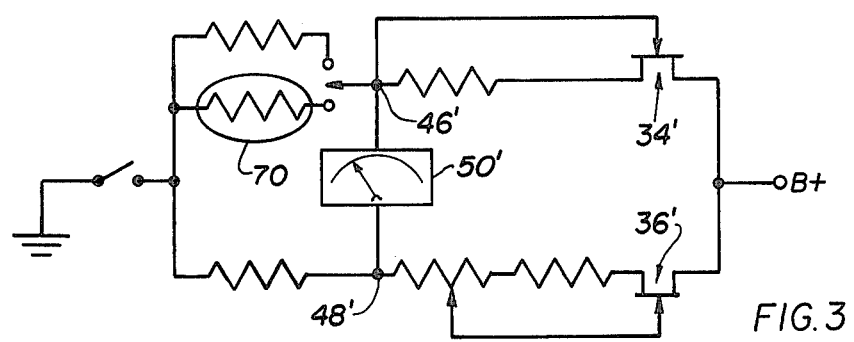
FIG. 3 is a schematic illustration of an alternate form of the circuit of FIG. 2.

In FIG. 3 where like numerals indicate like parts this aforedescribed circuit is modified to use a thermister 70 as a temperature probe whose output will as with resistance detected by hand held probe 20 operate meter 50'. Such would allow one to monitor temperature of a person electronically. One could also employ a phototransistor in place of thermister 70.

Having described operative embodiments of this invention, the protection sought therefor by these Letters Patent is now set forth by a series of appended claims.

I claim:

1. A constant current temperature measuring apparatus comprising:
   a power source;
   leads from said source to provide separate paths for current flow, said paths being characterized as a first leg of the circuit and a second leg of the circuit;
   a first field effect transistor in said first leg of the circuit;
   a second field effect transistor in said second leg of the circuit;
   means connecting said source to the drain terminals of said first and second field effect transistors;
   resistance means in each of said first and second leg of the circuit, each said resistance means being connected to a respective source terminal of said first and second field effect transistors, said resistance means in said first leg including a variable resistance whose control arm is connected to the gate of said first field effect transistor and said resistance means in said second leg being connected to the gate of said second field effect transistor;
   a first terminal in said second leg of the circuit at the point of connection of said resistance means with the gate of said second field effect transistor;
   a second terminal in said first leg of the circuit after the variable resistance;
   an indicator connected between said first terminal and said second terminal; and
   means to recombine said separate paths of said first and second leg of the circuit, said means to recombine having a first switch in said second leg, a calibration means in said second leg beyond beyond said first switch, a probe device in said second leg, a resistor in said first leg, a lead connecting said first leg and said second leg and a second switch connecting the lead to the source in completion of the temperature measuring apparatus.

2. The apparatus of claim 1 further including a housing enclosing the circuits, said housing having means to preset the indicator for ease of viewing and means to accommodate said probe device so that the probe device may be readily removed and used remote of said housing.

3. The apparatus of claim 2 wherein the probe device is characterized as an electrically insulative body having spaced separate detectors with separate leads connected in said second leg of the circuit so as to be operative in said circuit to provide a resistance path determined by the resistance of the object between said detectors for operation of the indicator.

4. The apparatus of claim 3 wherein the probe device and calibration means are interchangeably connectable by the first switch to allow one or the other to be connected between said terminals of said first leg and said second leg about said indicator via the lead recombining the first leg and second leg.

* * * * *